US007416553B2

(12) United States Patent  
Patel et al.

(10) Patent No.: US 7,416,553 B2
(45) Date of Patent: Aug. 26, 2008

(54) DRILL GUIDE AND PLATE INSERTER

(75) Inventors: Tushar Patel, Potomac, MD (US); Eric D. Kolb, Quincy, MA (US); Jonathan Fanger, Fall River, MA (US); Richard Fessler, Winnetka, IL (US); Alan Crockard, London (GB); Todd Albert, Penn Valley, PA (US)

(73) Assignee: Depuy Acromed, Inc., Raynham, MA (US)

( * ) Notice: Subject to any disclaimer, the term of this patent is extended or adjusted under 35 U.S.C. 154(b) by 632 days.

(21) Appl. No.: 10/409,958

(22) Filed: Apr. 9, 2003

(65) Prior Publication Data

US 2004/0204710 A1  Oct. 14, 2004

(51) Int. Cl.
*A61B 17/70* (2006.01)
(52) U.S. Cl. ...................................... 606/61
(58) Field of Classification Search ............. 606/86–87, 606/90, 92–93, 96, 98, 104–105
See application file for complete search history.

(56) References Cited

U.S. PATENT DOCUMENTS

| 1,920,821 | A | 8/1933 | Stephanus |
| 2,466,023 | A | 4/1949 | Griffin |
| 2,486,303 | A | 10/1949 | Longfellow |
| 2,494,229 | A | 1/1950 | Wollpert et al. |
| 2,695,688 | A | 11/1954 | Wollpert et al. |
| 3,244,170 | A | 4/1966 | McElvenny |
| 3,463,148 | A | 8/1969 | Allgower et al. |
| 3,552,389 | A | 1/1971 | Allgower et al. |
| 3,596,656 | A | 8/1971 | Kaute et al. |
| 3,659,595 | A | 5/1972 | Haboush |

(Continued)

FOREIGN PATENT DOCUMENTS

DE  4201043  1/1992

(Continued)

OTHER PUBLICATIONS

Product Literature, by SYNTHES Spine, *The Cervical Spine Locking Plate CSLP*, 2000.

(Continued)

*Primary Examiner*—Eduardo C. Robert
*Assistant Examiner*—Nicholas Woodall
(74) *Attorney, Agent, or Firm*—Nutter McLennen & Fish LLP

(57) ABSTRACT

A drill guide for use in securing a spinal fixation plate to a spine is provided. In a preferred embodiment, the drill guide generally includes a support member having first and second arms mated thereto. Each arm includes a proximal end and a distal end having at least one barrel coupled thereto and defining a lumen for receiving a tool. One or both arms can be slidably movable along the support member to allow the distance between the arms to be adjusted. In use, the arms can be adjusted to engage a spinal fixation plate and to position the barrels on each arm in alignment with bores formed in the fixation plate. The drill guide can then be used to drill, awl, tap, and insert implants, such as spinal screws, into the vertebral bodies to attach the fixation plate thereto.

13 Claims, 7 Drawing Sheets

U.S. PATENT DOCUMENTS

| | | | |
|---|---|---|---|
| 3,695,259 A | 10/1972 | Yost | |
| 3,716,050 A | 2/1973 | Johnston | |
| 3,779,240 A | 12/1973 | Kondo et al. | |
| 3,824,995 A | 7/1974 | Getscher et al. | |
| 3,900,025 A | 8/1975 | Barnes, Jr. | |
| RE28,841 E | 6/1976 | Allgower et al. | |
| 4,119,092 A | 10/1978 | Gil | |
| 4,187,841 A | 2/1980 | Knutson | |
| 4,219,015 A | 8/1980 | Steinemann et al. | |
| 4,224,699 A | 9/1980 | Weber et al. | |
| 4,257,411 A * | 3/1981 | Cho | 606/96 |
| 4,388,921 A | 6/1983 | Sutter et al. | |
| 4,408,601 A | 10/1983 | Wenk et al. | |
| 4,454,876 A | 6/1984 | Mears | |
| RE31,628 E | 7/1984 | Allgower et al. | |
| 4,493,317 A | 1/1985 | Klaue | |
| 4,502,475 A | 3/1985 | Weigle et al. | |
| 4,503,848 A | 3/1985 | Caspar et al. | |
| 4,513,744 A | 4/1985 | Klaue et al. | |
| 4,524,765 A | 6/1985 | de Zbikowski et al. | |
| 4,541,424 A * | 9/1985 | Grosse et al. | 606/98 |
| 4,651,724 A | 3/1987 | Berentey et al. | |
| 4,686,972 A | 8/1987 | Kurland | |
| 4,733,657 A * | 3/1988 | Kluger | 606/61 |
| 4,744,353 A | 5/1988 | McFarland | |
| 4,773,402 A | 9/1988 | Asher et al. | |
| 4,800,874 A | 1/1989 | David et al. | |
| 4,838,252 A | 6/1989 | Klaue et al. | |
| 4,848,327 A * | 7/1989 | Perdue | 606/54 |
| 4,936,844 A | 6/1990 | Chandler et al. | |
| 4,957,495 A * | 9/1990 | Kluger | 606/58 |
| 5,002,544 A | 3/1991 | Klaue et al. | |
| 5,006,120 A | 4/1991 | Carter | |
| 5,041,113 A | 8/1991 | Biedermann et al. | |
| 5,041,114 A | 8/1991 | Chapman et al. | |
| 5,041,133 A | 8/1991 | Sayano et al. | |
| 5,052,373 A * | 10/1991 | Michelson | 600/217 |
| 5,053,036 A | 10/1991 | Perren et al. | |
| 5,059,194 A * | 10/1991 | Michelson | 606/61 |
| 5,067,477 A | 11/1991 | Santangelo | |
| 5,088,472 A * | 2/1992 | Fakhrai | 600/214 |
| 5,129,899 A | 7/1992 | Small et al. | |
| 5,129,903 A | 7/1992 | Luhr et al. | |
| 5,147,361 A | 9/1992 | Ojima et al. | |
| 5,151,103 A | 9/1992 | Tepic et al. | |
| 5,180,381 A | 1/1993 | Aust | |
| 5,234,290 A | 8/1993 | Collins | |
| 5,275,601 A | 1/1994 | Gogolewski et al. | |
| 5,303,694 A | 4/1994 | Mikhail | |
| 5,318,567 A | 6/1994 | Vichard et al. | |
| 5,324,290 A | 6/1994 | Zdeblick et al. | |
| 5,336,224 A | 8/1994 | Selman | |
| 5,364,399 A | 11/1994 | Lowery et al. | |
| 5,365,921 A * | 11/1994 | Bookwalter et al. | 600/232 |
| 5,415,660 A | 5/1995 | Campbell et al. | |
| 5,423,826 A | 6/1995 | Coates et al. | |
| 5,439,463 A | 8/1995 | Lin | |
| 5,501,684 A | 3/1996 | Schlapfer et al. | |
| 5,520,690 A | 5/1996 | Errico et al. | |
| 5,531,746 A | 7/1996 | Errico et al. | |
| 5,531,751 A | 7/1996 | Schultheiss et al. | |
| 5,534,027 A | 7/1996 | Hodorek | |
| 5,549,612 A | 8/1996 | Yapp et al. | |
| 5,558,622 A | 9/1996 | Greenberg | |
| 5,578,034 A | 11/1996 | Estes | |
| 5,601,553 A | 2/1997 | Trebing et al. | |
| 5,603,713 A | 2/1997 | Aust | |
| 5,607,426 A | 3/1997 | Ralph et al. | |
| 5,607,428 A | 3/1997 | Lin | |
| 5,616,142 A | 4/1997 | Yuan et al. | |
| 5,616,144 A | 4/1997 | Yapp et al. | |
| 5,643,265 A | 7/1997 | Errico et al. | |
| 5,651,283 A | 7/1997 | Runciman et al. | |
| 5,669,915 A | 9/1997 | Caspar et al. | |
| 5,672,177 A | 9/1997 | Seldin | |
| 5,676,666 A * | 10/1997 | Oxland et al. | 606/61 |
| 5,713,904 A | 2/1998 | Errico et al. | |
| 5,735,853 A | 4/1998 | Olerud | |
| 5,745,884 A | 4/1998 | Carnegie et al. | |
| 5,749,873 A | 5/1998 | Fairley et al. | |
| 5,749,884 A | 5/1998 | Benderev et al. | |
| 5,755,721 A | 5/1998 | Hearn | |
| 5,788,630 A * | 8/1998 | Furnish | 600/232 |
| 5,807,396 A | 9/1998 | Raveh et al. | |
| 5,827,286 A | 10/1998 | Incavo et al. | |
| 5,846,193 A * | 12/1998 | Wright | 600/215 |
| 5,851,207 A | 12/1998 | Cesarone | |
| 5,865,848 A | 2/1999 | Baker | |
| 5,876,402 A | 3/1999 | Errico et al. | |
| 5,885,286 A | 3/1999 | Sherman et al. | |
| 5,888,204 A | 3/1999 | Ralph et al. | |
| 5,904,683 A | 5/1999 | Pohndorf et al. | |
| 5,931,838 A | 8/1999 | Vito | |
| 5,951,558 A | 9/1999 | Fiz et al. | |
| 5,954,722 A | 9/1999 | Bono | |
| 5,964,762 A | 10/1999 | Biedermann et al. | |
| 5,964,763 A | 10/1999 | Incavo et al. | |
| 5,967,171 A | 10/1999 | Dwyer, Jr. | |
| 5,984,926 A | 11/1999 | Jones | |
| 6,006,581 A | 12/1999 | Holmes | |
| 6,017,345 A | 1/2000 | Richelsoph | |
| 6,030,389 A | 2/2000 | Wagner et al. | |
| 6,039,740 A | 3/2000 | Olerud et al. | |
| 6,063,090 A | 5/2000 | Schlapfer et al. | |
| 6,066,142 A | 5/2000 | Serbousek et al. | |
| 6,066,175 A | 5/2000 | Henderson et al. | |
| 6,106,527 A | 8/2000 | Wu et al. | |
| 6,113,602 A | 9/2000 | Sand | |
| 6,117,173 A | 9/2000 | Taddia et al. | |
| 6,132,432 A | 10/2000 | Richelsoph | |
| 6,139,550 A | 10/2000 | Michelson | |
| 6,152,927 A | 11/2000 | Farris et al. | |
| 6,159,244 A | 12/2000 | Suddaby | |
| 6,193,721 B1 * | 2/2001 | Michelson | 606/70 |
| 6,200,348 B1 | 3/2001 | Biedermann et al. | |
| 6,206,828 B1 * | 3/2001 | Wright | 600/232 |
| 6,206,881 B1 | 3/2001 | Frigg et al. | |
| 6,224,602 B1 | 5/2001 | Hayes | |
| 6,227,124 B1 | 5/2001 | Gaydos et al. | |
| 6,228,085 B1 | 5/2001 | Theken et al. | |
| 6,235,033 B1 | 5/2001 | Brace et al. | |
| 6,235,034 B1 | 5/2001 | Bray | |
| 6,241,731 B1 | 6/2001 | Fiz et al. | |
| 6,258,092 B1 | 7/2001 | Dall et al. | |
| 6,258,098 B1 | 7/2001 | Taylor et al. | |
| 6,261,291 B1 | 7/2001 | Talaber et al. | |
| 6,273,889 B1 | 8/2001 | Richelsoph | |
| 6,277,124 B1 | 8/2001 | Haag | |
| 6,293,949 B1 | 9/2001 | Justis et al. | |
| 6,306,136 B1 | 10/2001 | Baccelli et al. | |
| 6,306,139 B1 | 10/2001 | Fuentes et al. | |
| 6,309,393 B1 | 10/2001 | Tepic et al. | |
| 6,322,562 B1 | 11/2001 | Wolter et al. | |
| 6,328,738 B1 | 12/2001 | Suddaby | |
| 6,331,179 B1 | 12/2001 | Freid et al. | |
| 6,332,887 B1 | 12/2001 | Knox | |
| 6,340,363 B1 * | 1/2002 | Bolger et al. | 606/90 |
| 6,342,055 B1 | 1/2002 | Eisermann et al. | |
| 6,342,056 B1 | 1/2002 | Mac-Thiong et al. | |
| 6,342,057 B1 | 1/2002 | Brace et al. | |
| 6,379,364 B1 * | 4/2002 | Brace et al. | 606/96 |
| 6,402,756 B1 | 6/2002 | Ralph et al. | |
| 6,413,259 B1 | 7/2002 | Lyons et al. | |
| 6,416,518 B1 | 7/2002 | DeMayo | |

| | | |
|---|---|---|
| 6,419,678 B1 | 7/2002 | Asfora |
| 6,428,542 B1 | 8/2002 | Michelson |
| 6,441,602 B1 | 8/2002 | Eckhardt et al. |
| 6,447,512 B1 | 9/2002 | Landry et al. |
| 6,454,769 B2 | 9/2002 | Wagner et al. |
| 6,503,250 B2 | 1/2003 | Paul |
| 6,527,776 B1 | 3/2003 | Michelson |
| 6,533,786 B1 * | 3/2003 | Needham et al. ............... 606/61 |
| 6,565,571 B1 | 5/2003 | Jackowski |
| 6,575,975 B2 | 6/2003 | Brace et al. |
| 6,585,738 B1 | 7/2003 | Mangione et al. |
| 6,592,586 B1 | 7/2003 | Michelson |
| 6,595,993 B2 | 7/2003 | Donno et al. |
| 6,602,255 B1 | 8/2003 | Campbell et al. |
| 6,602,257 B1 | 8/2003 | Thramann |
| 6,620,163 B1 | 9/2003 | Michelson |
| 6,641,613 B2 | 11/2003 | Sennett |
| 6,652,525 B1 | 11/2003 | Assaker et al. |
| 6,656,181 B2 | 12/2003 | Dixon et al. |
| 6,669,700 B1 | 12/2003 | Farris et al. |
| 6,679,883 B2 | 1/2004 | Hawkes et al. |
| 6,695,846 B2 | 2/2004 | Richelsoph et al. |
| 6,712,818 B1 | 3/2004 | Michelson |
| 6,755,833 B1 | 6/2004 | Paul et al. |
| 6,770,096 B2 * | 8/2004 | Bolger et al. ............ 623/17.16 |
| 6,793,658 B2 | 9/2004 | LeHuec et al. |
| 6,796,986 B2 | 9/2004 | Duffner |
| 7,011,665 B2 | 3/2006 | Null et al. |
| 7,094,242 B2 | 8/2006 | Ralph et al. |
| 7,147,599 B2 | 12/2006 | Phillips et al. |
| 2001/0009971 A1 * | 7/2001 | Sherts et al. ................ 600/231 |
| 2001/0021851 A1 | 9/2001 | Eberlein et al. |
| 2001/0037112 A1 | 11/2001 | Brace et al. |
| 2001/0047172 A1 | 11/2001 | Foley |
| 2002/0022843 A1 | 2/2002 | Michelson |
| 2002/0045897 A1 | 4/2002 | Dixon et al. |
| 2002/0045898 A1 | 4/2002 | Freid et al. |
| 2002/0049444 A1 | 4/2002 | Knox |
| 2002/0055741 A1 | 5/2002 | Schlapfer et al. |
| 2002/0058939 A1 | 5/2002 | Wagner et al. |
| 2002/0058940 A1 | 5/2002 | Frigg et al. |
| 2002/0082606 A1 | 6/2002 | Suddaby |
| 2002/0143336 A1 | 10/2002 | Hearn |
| 2002/0147450 A1 | 10/2002 | LeHuec et al. |
| 2002/0151899 A1 | 10/2002 | Bailey et al. |
| 2002/0156474 A1 | 10/2002 | Wack et al. |
| 2002/0183754 A1 | 12/2002 | Michelson |
| 2002/0183757 A1 | 12/2002 | Michelson |
| 2002/0188296 A1 | 12/2002 | Michelson |
| 2003/0023242 A1 | 1/2003 | Harrington |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0065251 A1 * | 4/2003 | Feng et al. ................... 600/229 |
| 2003/0083658 A1 | 5/2003 | Hawkes et al. |
| 2003/0135213 A1 | 7/2003 | LeHuec et al. |
| 2003/0181912 A1 | 9/2003 | Michelson |
| 2003/0187436 A1 * | 10/2003 | Bolger et al. .................. 606/61 |
| 2003/0187440 A1 | 10/2003 | Richelsoph et al. |
| 2003/0187442 A1 | 10/2003 | Richelsoph et al. |
| 2003/0187454 A1 | 10/2003 | Gill et al. |
| 2003/0208204 A1 | 11/2003 | Bailey et al. |
| 2003/0229348 A1 | 12/2003 | Sevrain |
| 2003/0233098 A1 | 12/2003 | Markworth |
| 2004/0015169 A1 | 1/2004 | Gause |
| 2004/0015174 A1 | 1/2004 | Null |
| 2004/0019353 A1 | 1/2004 | Freid et al. |
| 2004/0034352 A1 | 2/2004 | Needham et al. |
| 2004/0034354 A1 | 2/2004 | Paul |
| 2004/0087951 A1 | 5/2004 | Khalili |
| 2004/0092947 A1 | 5/2004 | Foley |
| 2004/0097935 A1 | 5/2004 | Richelsoph et al. |
| 2004/0133205 A1 | 7/2004 | Thramann et al. |
| 2005/0021040 A1 * | 1/2005 | Bertagnoli ..................... 606/90 |

FOREIGN PATENT DOCUMENTS

| | | |
|---|---|---|
| EP | 0897697 | 2/1999 |
| FR | 2827150 | 1/2003 |
| WO | WO-9632071 | 10/1996 |
| WO | WO-0022999 | 4/2000 |
| WO | WO-0064359 | 11/2000 |
| WO | WO-02085226 | 10/2002 |
| WO | WO 03/007826 | 1/2003 |
| WO | WO-03/024344 | 3/2003 |
| WO | WO-03063714 | 8/2003 |

OTHER PUBLICATIONS

Cervi-Lok™ Surgical Technique Manual (pp. 1-19), 1995 SPINTECH Inc.®, L1015 Revision B.

* cited by examiner

DRILL GUIDE AND PLATE INSERTER

FIELD OF THE INVENTION

The present invention relates to devices for assisting in spinal surgery, and more particularly to a drill guide and plate inserter for introducing spinal tools and devices.

BACKGROUND OF THE INVENTION

Advancing age, as well as injury, can lead to changes in the bones, discs, joints, and ligaments of the spine, producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is a bone fixation plate that is used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The openings are either holes or slots to allow for freedom of screw movement. The bone plate is placed against the damaged vertebral bodies and bone screws are used to secure the bone plate to the spine and optionally to a prosthetic implant or bone graft positioned between the adjacent vertebrae. Implantation of the plate, however, can be difficult. Each plate must be properly aligned with the vertebral bodies, and holes for receiving the bone screws must be drilled into the vertebrae at precise angles. It is often necessary to use the bone plate as a drill guide for drilling and tapping the bone in preparation for receiving the bone screws. Such a procedure can be difficult, however, as the surgeon is required to securely and rigidly hold the bone plate against the vertebrae, obtain proper alignment, drill, tap, and finally set the bone screws.

Accordingly, there remains a need for a drill guide instrument which can be used to assist in fastening a plate to a patient's spine.

SUMMARY OF THE INVENTION

The present invention generally provides a drill guide having a support member with first and second arms mated thereto. Each arm has a proximal end coupled to the elongate support member and a distal end having at least one guide member formed thereon. At least one of the guide members preferably includes at least one barrel that defines a lumen for receiving a tool. One or both of the first and second arms can be slidably movable along the support member to allow a distance between the first and second arms to be adjusted. In one embodiment, the first and second arms each include a proximal portion that extends in a direction substantially transverse to the support member, and a distal portion that extends at an angle with respect to the proximal portion.

While one or both guide member can have any number of barrels mated thereto, preferably at least one of the guide members has two barrels mated thereto. More preferably, the first and second arms are mated to a proximal portion of one of the two barrels, and the opposed distal end of the barrel is mated to a base plate. If a second barrel is provided, the second barrel is preferably mated to the base plate. Each base plate can optionally include a mating element formed thereon for mating with a spinal fixation plate, and/or for aligning the guide member with a spinal fixation plate. Each base plate can also optionally have a shape adapted to match the contour of a spinal fixation plate. Preferably, the mating element is formed on a distal surface of each base plate. The mating element can have a variety of configurations, and can be, for example, a protrusion extending distally from the distal surface of the base plate and adapted to engage a spinal fixation plate. Each protrusion is preferably oriented at an angle so that they are effective to grasp a spinal fixation plate when the first and second arms are moved either toward or away from one another.

As indicated above, one or both arms can be slidably movable along the support member. In an exemplary embodiment, the first arm is fixedly attached to the support member while the second arm is slidably movable. An adjustment mechanism can be formed on or mated to the proximal end of the second arm to allow movement of the second arm along the support member. The adjustment mechanism can comprise a spring-lock mechanism that is movable between a first, locked position, and a second position wherein the second arm is slidable along the support member. Alternatively, by way of non-limiting example, the adjustment mechanism can comprise threads formed on each of the support member and the second arm such that rotation of the support member is effective to move the second arm with respect to the first arm.

In yet another embodiment of the present invention, an adjustable guide member is provided having a first member with an elongate support and a first arm mated to one end thereof. The arm preferably extends in a direction transverse to the support and includes a first guide member mated to a distal end thereof. The adjustable guide member further includes a second member having a second arm with a first end adapted to slidably mate with and extend in a direction transverse to the elongate support of the first member. The second arm includes a second guide member mated to a distal end thereof. At least one of the guide members is preferably adapted to receive a tool therethrough.

Each of the first and second arms can include a proximal portion and a distal portion, and the proximal portion of each arm can extend in a direction substantially transverse to the elongate support of the first member, and the distal portion of each arm can extend at an angle with respect to the proximal portion. Preferably, at least one of the first and second guide members includes at least one barrel, which can optionally be removably mated to the first and/or second arms. Each barrel is preferably disposed at an angle with respect to spinal fixation plate adapted to be engaged by the drill guide. The angle of at least one of the barrels can optionally be adjustable.

In further aspects, the guide member on each arm can comprise a first barrel having a distal end and a proximal end mated to the distal end of the arm, and a base plate mated to the distal end of the first barrel. A second barrel can optionally be mated to the base plate. Each base plate preferably includes a mating element formed thereon for mating with a spinal fixation plate, and each base plate can have a shape adapted to match the contour of a spinal fixation plate. By way of non-limiting example, the mating element can be formed on a distal surface of each base plate, and can comprise a protrusion extending distally from the distal surface of the base plate and adapted to engage a spinal fixation plate. Preferably, each protrusion is oriented at an angle so that they are effective to grasp a spinal fixation plate when the arms are moved either toward or away from one another.

The adjustable drill guide can also optionally include an adjustment mechanism formed on or mated to the second member and effective to allow movement of the second member along the elongate support of the first member. While a variety of adjustment mechanisms can be used, in one embodiment the adjustment mechanism can comprise a box-shaped member having a spring-lock mechanism that is movable between a first, locked position, and a second position wherein the second support member is slidable along the first support member. The first arm can also optionally be slidably mated to the elongate support, and thus can include an adjustment mechanism formed thereon.

In another embodiment, the adjustable drill guide further includes a third arm mated to the first guide member and a fourth arm mated to the second guide member. Preferably, the first guide member comprises a frame having a first end mated to the first arm and a second, opposed end mated to the third arm, and the second guide member comprises a frame having a first end mated to the second arm and a second, opposed end mated to the fourth arm. The support member can optionally be movable between a first position, in which it is slidably mated to the first and second arms, and a second position, in which it is slidably mated to the third and fourth arms. The device can also optionally include a second support member mated to the third and fourth arms.

In yet another embodiment of the present invention, a spinal fixation kit is provided including a spinal fixation plate having a proximal portion with at least one bore formed therein for receiving a fixation device effective to mate the proximal portion to a first vertebrae, and a distal portion with at least one bore formed therein for receiving a fixation device effective to mate the distal portion to a second, adjacent vertebrae. The kit further includes a guide device having an elongate support member, a first arm having a proximal end mated to the elongate support member and a distal end with at least one guide member coupled thereto, the guide member being configured for juxtaposition on the proximal portion of the spinal fixation plate, and a second arm having a proximal end mated to the elongate support member and a distal end with at least one guide member coupled thereto, the guide member being configured for juxtaposition on the distal portion of the spinal fixation plate.

BRIEF DESCRIPTION OF THE DRAWINGS

The invention will be more fully understood from the following detailed description taken in conjunction with the accompanying drawings, in which.

DETAILED DESCRIPTION OF THE INVENTION

In general, the present invention provides a drill guide for use in securing a spinal fixation plate to a spine. The drill guide generally includes a support member having first and second arms mated thereto. Each arm includes a proximal end and a distal end having a guide member with at least one barrel coupled thereto and defining a lumen for receiving a tool. One or both arms can be slidably movable along the support member to allow the distance between the arms to be adjusted. In use, the arms can be adjusted to engage a spinal fixation plate and to position the barrels on each arm in alignment with bores formed in the fixation plate, thereby providing a fixed entry angle for tools being inserted through the barrels. The drill guide can then be used to drill, awl, tap, and insert implants, such as spinal screws, into the vertebral bodies to attach the fixation plate thereto. The drill guide is particularly advantageous in that it can function as a drill guide, a midline alignment device, as well as a plate inserter for a range of plate sizes. The device further provides a more time efficient and simplified surgical procedure, eliminating several unnecessary steps and instruments typically required to implant a cervical plate.

Figure 1:
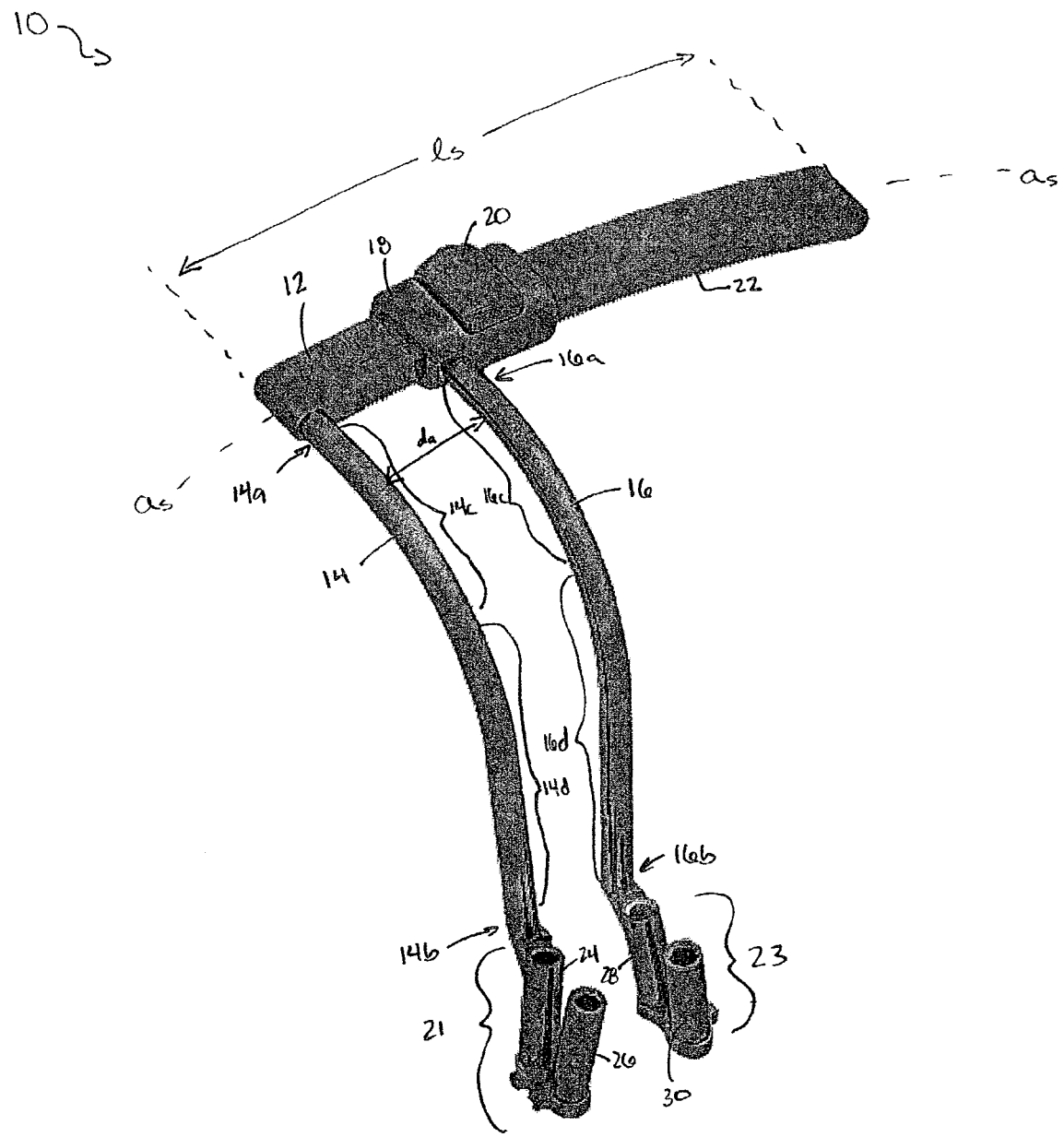
FIG. 1 is a perspective view of a drill guide according to one embodiment of the present invention.
Figure 2:
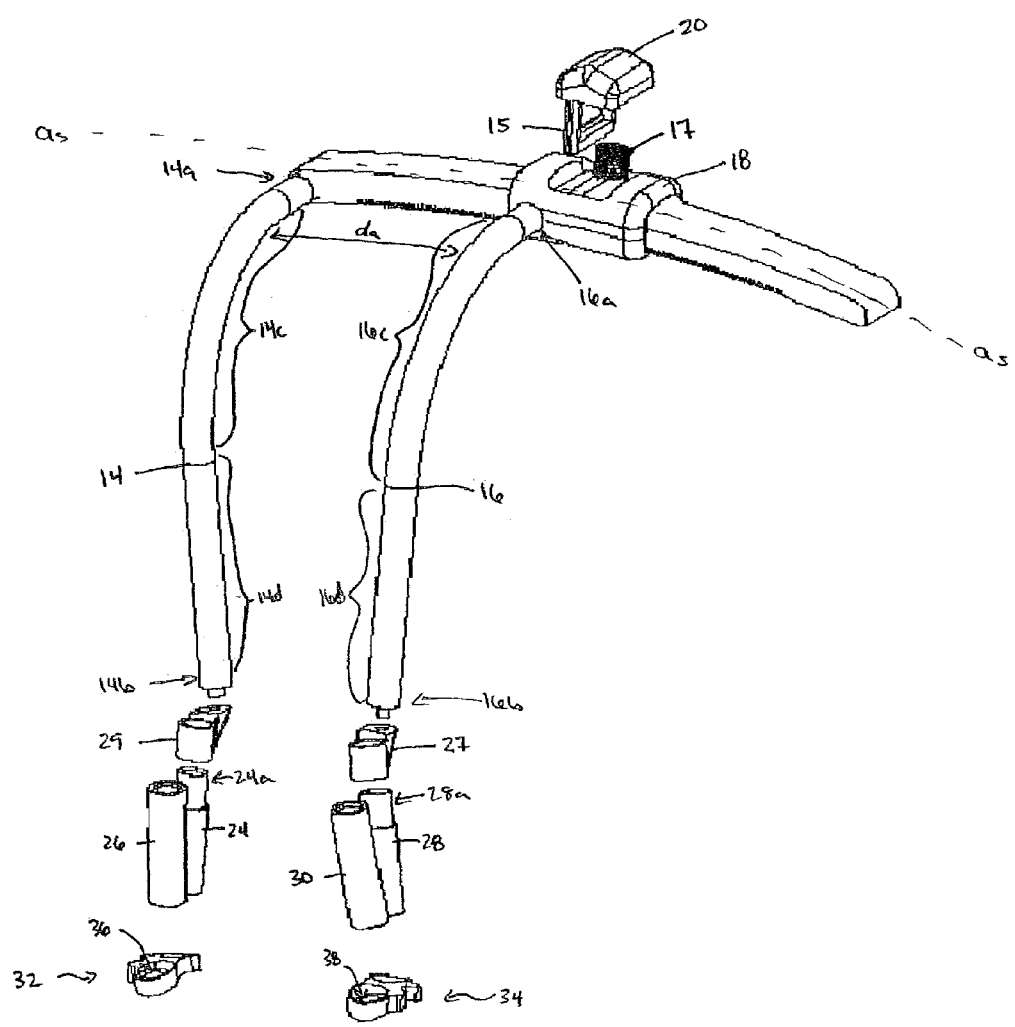
FIG. 2 is a perspective view of the drill guide shown in FIG. 1 in an unassembled state.

FIGS. 1 and 2 illustrate one embodiment of a drill guide 10 according to the present invention. As shown, the drill guide 10 includes an elongate support member 12 having first and second arms 14, 16 mated thereto, at least one of which is preferably slidably mated to the support member 12. Each arm 14, 16 includes a guide member 21, 23 mated to the distal end thereof for drilling, tapping, and inserting implants into vertebral bodies. The support member 12 can have a variety of shapes and sizes, but it preferably is an elongate member having a profile that is slightly curved along the longitudinal axis $a_s$ such that the profile is adapted to match the contour of a patient's spine. The curvature in the support member 12 facilitates the proper positioning of the guide members 21, 23 as the distance between the arms 14, 16 is adjusted, which will be discussed in more detail below. The support member 12 can have a variety of cross-sectional shapes such as, for example, square, circular, oval, rectangular, triangular, etc. The length $l_s$ of the support member 12 can also vary, but the length $l_s$ is preferably sufficient to allow the arms 14, 16 to move a distance $d_a$ apart from one another to engage a spinal fixation plate, as discussed below. In an exemplary embodiment, the length $l_s$ of the support member 12 is in the range of about 25 mm to 200 mm, and more preferably is about 100 mm to 150 mm. The support member 12 can also be adapted to mate to another support, such as a mounting rack (not shown) used during surgical procedures. A person having ordinary skill in the art will appreciate that the support member 12 can have a variety of configurations.

Still referring to FIGS. 1 and 2, the arms 14, 16 each include a proximal end 14a, 16a mated to the support member 12, and a distal end 14b, 16b. The proximal end 14a, 16a of one or both arms 14, 16 can be slidably mated to the support member 12. Preferably, as shown, one of the arms 14, 16, e.g., the first arm 14, is fixedly mated to one end of the support member 12, and the other arm 14, 16, e.g., the second arm 16, is slidably mated to the support member 12 and movable along the remaining length $l_s$ of the support member 12. A variety of mating techniques can be used to slidably mate the second arm 16 to the support member. By way of non-limiting example, FIGS. 1 and 2 illustrate a box-like housing 18 formed on or mated to the proximal end of the second arm 16 and having a push-button 20 disposed therein. The box-like housing 18 is adapted to fit around and slidably receive the support member 12, and the push-button 20 is effective to engage the support member 12 to prevent movement of the second arm 16. As shown in FIG. 2, the push-button 20 includes a substantially rectangular or square engagement member 15 that extends distally from the push-button 20. The engagement member 15 slidably receives the support member 12 and is effective to engage a series of ridges 22 formed on the support member 12. The push-button 20 further includes a spring 17 disposed therein for allowing the button 20 to be activated. In use, the spring 17 applies a force onto the push-button 20 to cause the engagement mechanism 15 to grasp the ridges 22 formed on the support member, thereby retaining the arm 16 in the locked position. The arm 16 can be moved by pressing down on the push-button 20 and thereby releasing the engagement mechanism 15 from the ridges 22. The arm 16 is then free to slide along the support member 12 while the button 20 is held in the down position. A person having ordinary skill in the art will appreciate that a virtually any technique can be used to allow slidable movement of the second arm 16 along the support member 12. Moreover, as previously stated, both arms 14, 16 can optionally be movable along the support member 12.

Each arm 14, 16 can have a variety of shapes and sizes, but preferably each arm 14, 16 has a generally elongate shape to allow the distal end 14b, 16b of each arm 14, 16 to be positioned at a surgical site while the support member 12 is positioned outside the surgical field. While the arms 14, 16 can be substantially straight, the arms 14, 16 are preferably curved to prevent the support member 12 from hindering or blocking the surgeon's view of the surgical site. In an exemplary embodiment, each arm 14, 16 includes a proximal portion 14c, 16c that extends in a direction substantially perpendicular to the longitudinal axis as of the support member 12, and a distal portion 14d, 16d that extends in a direction substantially perpendicular to the proximal portion 14c, 16c of the arms 14, 16. The proximal and distal sections 14c, 16c, 14d, 16d can be bent with respect to one another, but are preferably curved to provide a smooth profile. In an exemplary embodiment, the arms 14, 16 have a shape and size that does not require a large incision to be made in order to use the device. As shown in FIG. 1, for example, the arms 14, 16 have a generally small diameter and are curved slightly toward one another to allow each arm 14, 16 to be inserted through a relatively small incision. Moreover, the distal end of the guide member 21, 23 on each arm 14, 16 is positioned at a distance apart from one another that is greater than the distance between the proximal end of each guide member 21, 23. As a result, the distance required for the guide members 21, 23 to mate to a spinal fixation plate is slightly reduced.

A person having ordinary skill in the art will appreciate that each arm 14, 16 can have virtually any shape and size, and that FIGS. 1 and 2 only illustrate one preferred embodiment. Moreover, while FIGS. 1-4 illustrate a drill guide 10 having only two arms 14, 16, the guide 10 can include any number of arms (not shown) to allow the device to used with one or several spinal fixation plates. The drill guide can also include additional arms opposed to the first and second arms for allowing the support member to be positioned on one or both sides of a fixation plate being engaged by the drill guide 10, as will be described in more detail with respect to FIG. 6.

The distal end 14b, 16b of each arm 14, 16 is preferably adapted to mate to or engage a spinal fixation plate, and can thus can include a drill guide member 21, 23 formed thereon or mated thereto. Each drill guide member 21, 23 can have a variety of configurations, but at least one of the drill guide members 21, 23 preferably includes one or more barrels mated thereto for receiving a tool, as will be described in more detail below. The arms 14, 16 can be fixedly mated to the drill guide members 21, 23, or alternatively they can be removably mated to the drill guide members 21, 23. Moreover, the arms 14, 16 can be mated to any portion of the drill guide members 21, 23. Preferably, where the drill guide member 21, 23, includes a barrel mated thereto, the arm 14, 16 is mated to a proximal end 24a, 26a, 28a, 30a of one of the barrels 24, 26, 28, 30. As shown in FIG. 2, the distal end 14b, 16b of each arm can mate to an extension member 29, 27, which preferably extends in a direction transverse to the arm 14, 16. As is further shown in FIG. 2, the proximal end 24a of barrel 24 is mated to extension member 29, and the proximal end 28a of barrel 28 is mated to extension 27. As a result, the arms 14, 16 are offset with respect to the barrels 24, 26, 28, 30 to provide better visual access to the surgical site. A person having ordinary skill in the art will appreciate that the arms can be mated to any portion of the guide members 21, 23, and alternatively the arms 14, 16 can be adapted for use in other surgical procedures.

Figure 3A:
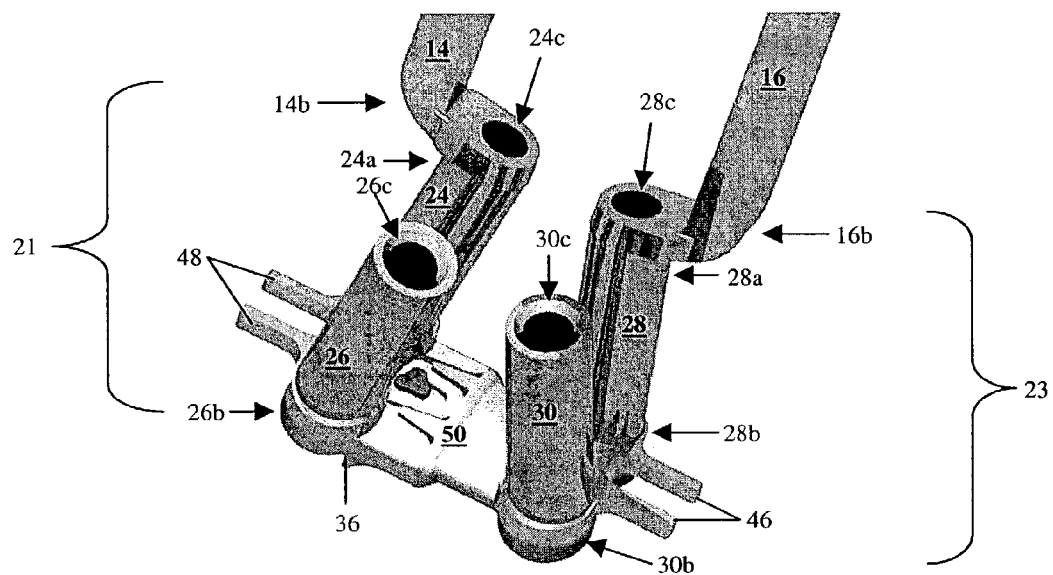
FIG. 3A is a perspective view of the drill guide member portion of the drill guide shown in FIG. 1.
Figure 3B:
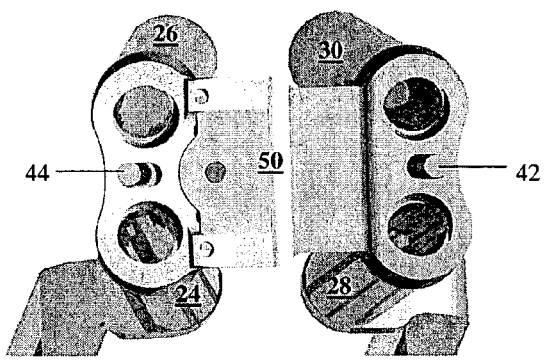
FIG. 3B is a perspective view of the distal end of the drill guide member shown in FIG. 3A.

FIGS. 3A-3B illustrate the drill guide members 21, 23 in more detail. While each drill guide member 21, 23, can have a variety of configurations, at least one of the guide members 21, 23 preferably includes one or more barrels 24, 26, 28, 30 mated thereto. The barrels 24, 26, 28, 30 can be removably or fixedly mated to one another and/or to the guide members 21, 23. Removable barrels 24, 26, 28, 30 are particularly advantageous in that they allow barrels having different lengths to be selected based on the intended use.

As shown in FIGS. 3A-3B, each guide member 21, 23 includes two barrels 24, 26, 28, 29 mated thereto. Each barrel 24, 26, 28, 30 can have a variety of shapes and sizes, but they should be adapted to receive a tool, such as awl, a drill bit, a fastener, or a driver device. In the embodiment shown in FIGS. 1-3B, each barrel 24, 26, 28, 30 has a generally cylindrical shape and includes a proximal end 24a, 26a, 28a, 30a, a distal end 24b, 26b, 28b, 30b, and an inner lumen 24c, 26c, 28c, 30c extending therebetween. A base plate 32, 34 extends between the distal ends 24b, 26b, 28b, 30b of each set of barrels to mate the barrels 24, 26, 28, 30 to one another, and the proximal end of one of the two barrels, e.g., barrel 24a and barrel 28a, is mated to the distal end 14b, 16b of an arm 14, 16. The base plates 32, 34 that mate the barrels 24, 26, 28, 30 can optionally include bores (not shown) formed therein for removably or fixedly receiving the barrels 24, 26, 28, 30.

The base plates 32, 34 can have a variety of configurations, but preferably each base plate 32, 34, or at least a distal surface of each base plate 32, 34, has a shape adapted to match the contour of a spinal fixation plate. Each base plate 32, 34 should also have a shape and size that results in the alignment of the barrels 24, 26, 28, 30 with corresponding bores formed in a spinal fixation plate being engaged by the drill guide.

The barrels 24, 26, 28, 30 are preferably disposed at a predetermined angle a with respect to the base plates 32, 34, or alternatively the base plates 32, 34 have a shape that causes the barrels 24, 26, 28, 30 to be positioned at an angle a with respect to a spinal fixation plate being engaged by the drill guide 10. The angle a of each barrel 24, 26, 28, 30 is determinative of the entry angle a of a tool or device being inserted therethrough, and thus the angle a should be set based on the intended use. The angle a of one or more of the barrels 24, 26, 28, 30 can also optionally be adjustable. In an exemplary embodiment, each barrel 24, 26, 28, 30 is positioned so that it is aligned with an axis of a corresponding bore formed in the spinal fixation plate 50 adapted to be engaged by the drill guide 10.

Each base plate 32, 34 can also be adapted to engage a spinal fixation plate 50, and thus can include one or more mating elements formed thereon. While a variety of mating elements can be used to mate each drill guide member 21, 23 to a spinal fixation plate, FIG. 3B illustrates one embodiment of a mating element 42, 44 formed on each base plate 32, 34. As shown, the mating elements each comprise a protrusion or pin member 42, 44 that extends from the distal surface of each base plate 32, 34. The pin members 42, 44 are adapted to extend into corresponding detents or bores formed along the midline of a fixation plate. Upon movement of the arms 14, 16 away from one another, the pin members 42, 44 engage the plate 50. The pin members can optionally be in the form of a hook or similar device effective to grasp the plate. The pin members 42, 44 can also optionally extend at an angle, preferably toward one another, to further facilitate grasping of the fixation plate 50. A person having ordinary skill in the art will appreciate that a variety of techniques can be used to mate the drill guide 10 to a spinal fixation plate 50. Moreover, the mating element can be adapted to grasp any portion of a fixation plate. By way of non-limiting example, other suitable mating techniques include a snap-fit engagement, a magnetic engagement, an interference fit, and any other mechanical connection.

Figure 4:
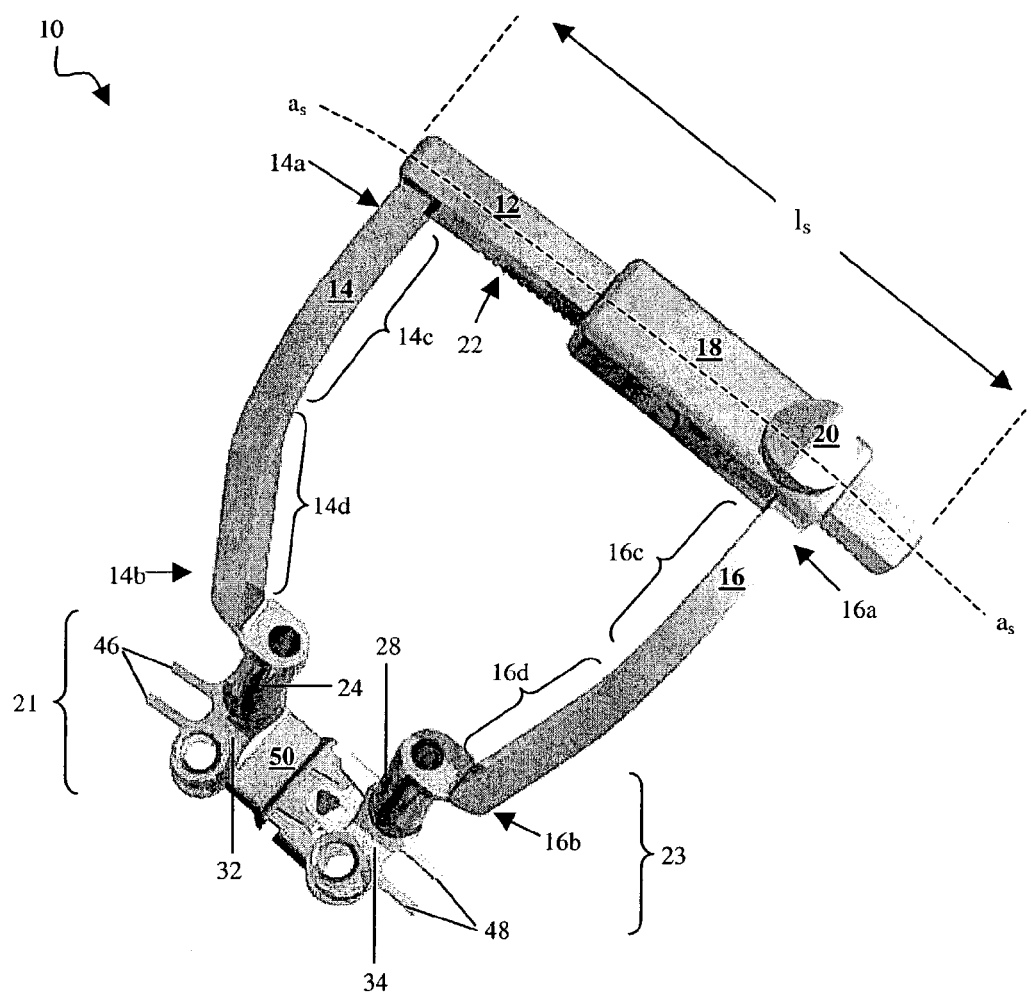
FIG. 4 is a perspective view of a drill guide according to the present invention having a spinal fixation plate mated thereto.

Each plate 32, 34 can also optionally include an alignment feature for aligning the drill guide 10 during implantation of a fixation plate 50. While a variety of alignment features can be used, in an exemplary embodiment the alignment feature is a fork member 46, 48, as shown in FIGS. 3A and 4, that extends outwardly from each drill guide member 21, 23. Typically, during implantation of a spinal fixation plate, Caspar pins are inserted into adjacent vertebral bodies and are used to distract the vertebrae. The Caspar pins can be left in place while the plate is being secured to the vertebrae, thereby allowing the fork-like members 46, 48 on drill guide 10 to be placed around the Caspar pins to facilitate positioning of the plate.

In another embodiment, the alignment mechanism can be formed on one or both guide members 21, 23 and can be effective to align the guide member 21, 23 with the endplate of a vertebral body. FIG. 3 illustrates a fin 36 formed on a distal surface of one side of spinal fixatin plate 50. A similar type of fin 36 can optionally be formed on one or both of the guide members 21, 23. Preferably, the fin 36 is formed on the guide member 21 that is positioned adjacent the superior endplate, rather than the inferior endplate. In use, the fin 36 abuts the endplate to align the guide members 21, 23 with the adjacent vertebrae.

FIG. 4 illustrates the drill guide 10 in use. As shown, the first and second arms 14, 16 can be positioned with respect to one another to grasp a fixation plate 50. A variety of fixation plates 50 can be used with the present invention, including fixation plates having an adjustable size. While the drill guide 10 can be adapted to position the guide member 21, 23 at different locations on a fixation plate, preferably one of the guide members, e.g., guide member 21, is positioned on the superior end of a fixation plate, and the other guide member, e.g., guide member 23, is positioned on the inferior end of a fixation plate. This is particularly advantageous in that a fixation plate can be fastened to adjacent vertebrae using a single drill guide that does not need to be repositioned during use. An even further advantage is provided where the device includes several arms, as several guide members can be positioned along a length of a patient's spine to fasten one or more fixation plates to one or more adjacent vertebrae without the need to reposition the device during use. As previously described above, the plate 50 can be grasped by positioning the mating element 42, 44 formed on each drill guide 21, 23 within corresponding detents or bores formed in the fixation plate 50. The arms 14, 16 are then moved away from one another, by pressing on the push-button 20, to grasp the fixation plate 50. Where a plate having an adjustable length is used, the arms 14, 16 can be moved to adjust the length of the plate, as desired. The support member can optionally include a measurement gauge for setting the length of the fixation plate, if necessary. If provided, and if Caspar pins are used during the surgery, the fork-like members 48, 46 can be placed around the Caspar pins to position the plate 50 with respect to the adjacent vertebrae. One or more of the barrels 24, 26, 28, 30, and/or the bores (not shown) formed in the base plates 32, 34, can be used to drill, awl, tap, and insert tools and implants, such as spinal screws, to secure the fixation plate 50 to the adjacent vertebrae.

A person having ordinary skill in the art will appreciate that while FIGS. 1-4 illustrate arms 14, 16 having guide member 21, 23 with two barrels 24, 26, 28, 30 mated thereto, the device 10 can have a variety of configurations. By way of non-limiting example, only one of the two arms 14, 16 can include a guide member 21, 23 formed thereon, and the guide member 21, 23 can include any number of barrels 24, 26, 28, 30 and/or guide bores formed therein. Alternatively, one or both arms can form the guide member and can include a bore extending therethrough for receiving a tool. Where the arm is curved, the bore preferably extends through the straightened distal portion of the arm.

Figure 5:
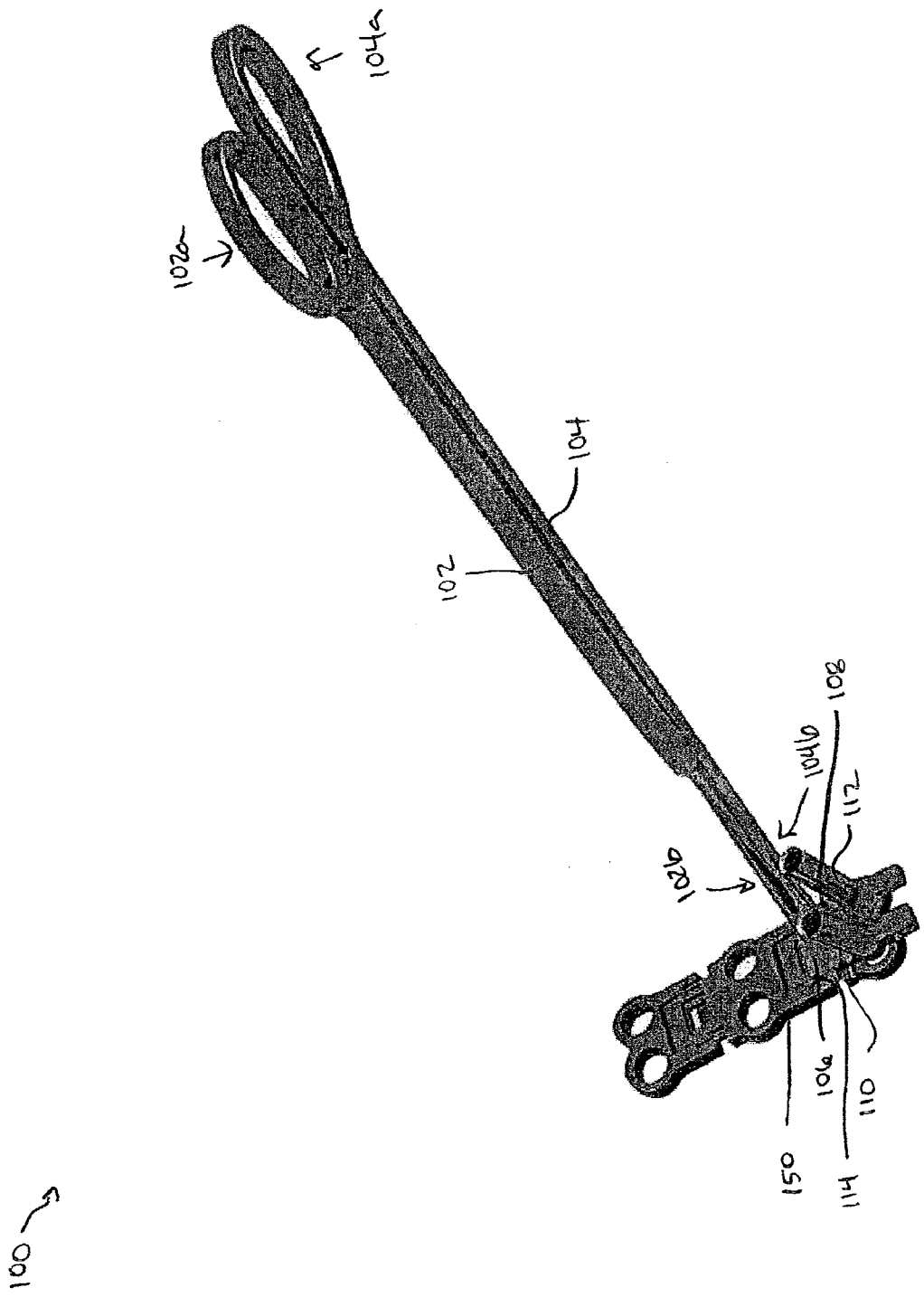
FIG. 5 is a perspective view of another embodiment of a drill guide according to the present invention.

FIG. 5 illustrates another embodiment of a drill guide 100 according to the present invention. As shown, the drill guide 100 includes first and second arms 102, 104 pivotally coupled to one another and movable between an open position (not shown) and a closed position, as shown. Each arm 102, 104 has a proximal, handle end 102a, 104a and a distal end 102b, 104b. A variety of handle members can be used to grasp the arms 102, 104. As shown, the handle members are in the form of loops 103, 105, similar to scissor handles. The arms 102, 104 can have a variety of configurations, but are preferably generally elongate and are effective to allow movement of the distal ends 102b, 104b toward and away from one another. A first guide member is mated to the distal end 102b of the first arm 102 and has a base plate 106 with a barrel 110 formed thereon for receiving a tool. The second guide member is mated to the distal end 104b of the second arm 104 and also has a base plate 108 and a barrel 112 formed thereon for receiving a tool.

Each base plate 106, 108 can have a variety of configurations, but preferably they are adapted to grasp a spinal fixation plate 150. As shown in FIG. 5, each base plate 106, 108 includes a hook-shaped member 114 (only one hook is shown) that is effective to fit around an edge of the fixation plate 150. In use, the hook members 114 come together to grasp opposed edges of the fixation plate 150 when the first and second arms are positioned in the closed position. Each base plate 106, 108 can also include an alignment mechanism for aligning the fixation plate 150 during implantation. The alignment mechanism is similar to alignment mechanisms 48 and 46 previously described above with respect to FIG. 3A, and can be in the form of a cut-out portion which, when the base plates 106, 108 are combined, form a U-shaped portion that is effective to fit around a Caspar pin.

The barrels 110, 112 can be fixedly attached to or removably mated to each base plate 106, 108, and each base plate 106, 108 can optionally include more than one barrel 110, 112. The barrels 110, 112 are similar to barrels 24, 26, 28, 30 described above with respect to FIGS. 1-4, and thus are preferably positioned at a predetermined angle which is determinative of the entry angle of a tool or implant being introduced into the barrel 110, 112. Alternatively, as was also described above, the base plates 106, 108 themselves can be angled to position the barrels at the desired angle with respect to the fixation plate 150.

In use, the arms 102, 104 are moved to the open position and the base plates 106, 108 are positioned on opposed edges of a fixation plate 150. The arms are then moved to the closed position, thereby causing the base plates 106, 108 to grasp the fixation plate 150. The barrels 110, 112 are thereby aligned with the corresponding bores formed in the fixation plate 150, and can be used to drill, awl, tap, and insert tools and implants, such as spinal screws, to secure the fixation plate 150 to the adjacent vertebrae.

A person having ordinary skill in the art will appreciate that the barrels 110, 112 of the drill guide 100 shown in FIG. 5 can each be mated to one arm, e.g., arm 104, and the other arm 102 can merely include a base plate 106 formed thereon. Moreover, the device 100 can include any number of barrels or other guide members formed on one or both arms 102, 104.

Figure 6:
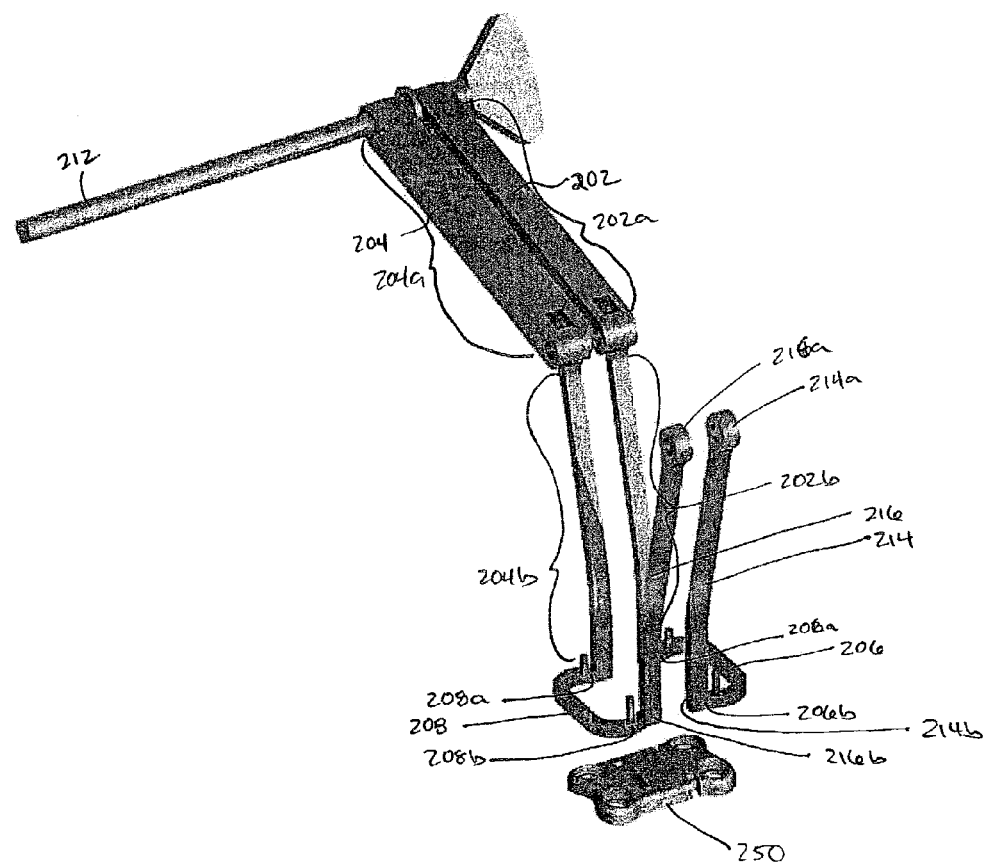
FIG. 6 is a perspective view of yet another embodiment of a drill guide according to the present invention.

FIG. 6 illustrates yet another embodiment of a drill guide 200. As shown, the drill guide 200 includes a linear support 212 having first and second arms 202, 204 mated thereto. One or both of the arms 202, 204 can be slidably mated to the support, but in an exemplary embodiment one of the arms, e.g., the first arm 202, is fixedly attached to the support 212, and the other arm, e.g., the second arm 204, is slidably mated to the support. While not shown, the second arm 204 can optionally include an adjustment mechanism, similar to adjustment mechanism 20 described above with respect to FIGS. 1, 2, and 4, for allowing the position of the arm 204 to be adjusted along the length of the support 212. In an exemplary embodiment, the adjustment mechanism comprises threads formed on the support member 212 and formed within a lumen extending through the proximal end of the second arm 204. In this embodiment, the first arm 202 should be freely rotatable with respect to the support member 212. In use, rotation of the support member 212 is effective to move the second arm 204 with respect to the first arm 202. In another embodiment (not shown), the rotating knob can be coupled to the second arm 204 and can, upon rotation, be effective to move the second arm 204 along the support 212. A person having ordinary skill in the art will appreciate that virtually any adjustment mechanism can be used to move one or both arms 202, 204 with respect to the support 212.

Each arm 202, 204 can have a variety of configurations, but preferably each arm 202, 204 includes a proximal portion 202a, 204a that extends in a direction substantially transverse to the support member 212, and a distal portion 202b, 204b that extends in a direction substantially transverse to the proximal portion 202a, 204a. The proximal portions 202a, 204a are preferably pivotally mated to the distal portions 202b, 204b to allow the angle of the portions with respect to one another to be adjusted. The distal-most end of each arm 202, 204 is mated to a guide member which is adapted to engage a spinal fixation plate 250. Each guide member can have a variety of configurations, but is preferably a frame 206, 208 having a first end 206a, 208a, and a second, opposed end 206b, 208b. The first end 206a, 208a of each frame 206, 208 is mated to the distal end of the arm 204, 202, respectively.

The device 200 can also include third and fourth arms 214, 216 each having a distal end 214b, 216b mated to the second end 206b, 208b of the frames 206, 208. The third and fourth arms 214, 216 are preferably the same as the distal portion 202b, 204b of the first and second arms 202, 204, however the third and fourth arms 214, 216 are adapted to be positioned on opposed sides of a spinal fixation plate 250 from the first and second arms 202, 204. The third and fourth arms 214, 216 can each optionally include a proximal portion (not shown) mated to a second support member (not shown). Alternatively, the proximal portions 202a, 204a of the first and second arms 204, 202 can be removably mated to the distal portions 202b, 204b, thereby allowing the proximal portion 202a, 204a of the first and second arms 202, 204 to be removed from the distal portion 202b, 204b of the first and second arms 202, 204 and to be attached to the third and fourth arms 214, 216. The use of a movable support member, or two support members, is particularly advantageous in that it allows the surgeon to operate from either side of the patient.

The frame 206, 208 on each arm 202, 204 can be adapted to mate to a spinal fixation plate, and can optionally be adapted to receive one or more barrels (not shown). In an exemplary embodiment, each frame 206, 208 has a shape that is adapted to fit around the outer perimeter of a spinal fixation plate 250. In use, the arms 202, 204 can be moved toward one another along the support 212 to cause the frames 206, 208 to grasp the plate by friction fit. Once engaged, one or more barrels can be attached to the frames 206, 208 to drill, awl, tap, and insert tools and/or implants therethrough to secure the plate to adjacent vertebrae.

Figure 7:
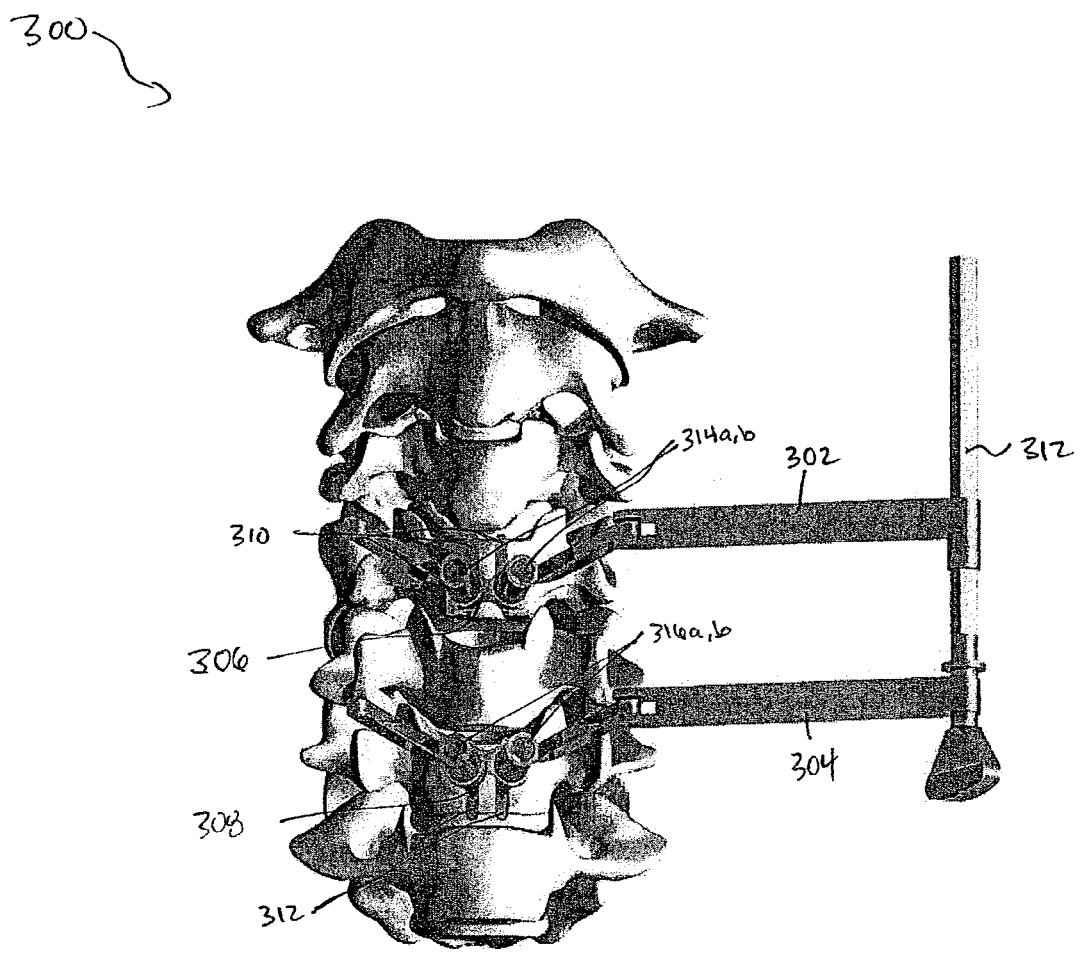
FIG. 7 is a perspective view of another embodiment of a drill guide according to the present invention shown positioned in a patient's spine.

FIG. 7 illustrates yet another embodiment of a drill guide 300 positioned along a portion of a patient's spinal column. The drill guide 300 is similar to drill guide 200, but it does not include frames 206, 208 that are adapted to engage a fixation plate. Rather, each arm 302, 304 includes a guide member having a base plate 306, 308 with two barrels 314a, 314b, 316a, 316b disposed thereon. Each base plate 306, 308 can also include an alignment mechanism, such as a fork-like member 310, 312, formed thereon for aligning the guide members with respect to Caspar pins. A fixation plate can then be aligned and fastened to the vertebrae using one or more spinal screws.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal fixation kit, comprising:
 a spinal fixation plate having
  a proximal portion with at least one bore formed therein for receiving a fixation device effective to mate the proximal portion to a first vertebrae, and
  a distal portion with at least one bore formed therein for receiving a fixation device effective to mate the distal portion to a second, adjacent vertebrae; and
 a guide device having
  an elongate support member,
  a first arm having a proximal end mated to the elongate support member and a distal end with at least one guide member coupled thereto, the guide member being configured for juxtaposition on the proximal portion of the spinal fixation plate, and a second arm having a proximal end mated to the elongate support member and a distal end with at least one guide member coupled thereto, the guide member being configured for juxtaposition on the distal portion of the spinal fixation plate, wherein at least one of the first and second arms is slidably movable along the elongate support member to adjust a distance between the first and second arms such that at any position along the elongate support member the spacing between the first and second arms remains substantially constant at any distance along the first and second arms, and wherein the guide member on each arm comprises a first barrel having a distal end and a proximal end mated to the distal end of the arm and a second barrel mated to a base plate, and wherein the base plate is mated to the distal end of the first barrel.

2. The spinal fixation kit of claim 1, wherein the elongate support member is curved to match the contour of a patient—s spine.

3. The spinal fixation kit of claim 1, wherein each of the first and second arms includes a proximal portion and a distal portion, and wherein the proximal portion of each arm extends in a direction substantially transverse to the support member, and wherein the distal portion of each arm extends at an angle with respect to the proximal portion.

4. The spinal fixation kit of claim 1, wherein the guide member on at least one of the arms includes at least one barrel.

5. The spinal fixation kit of claim 4, wherein the at least one barrel is disposed at an angle with respect to the spinal fixation plate.

6. The spinal fixation kit of claim 4, wherein the angle of the at least one barrel is adjustable.

7. The spinal fixation kit of claim 1, wherein each base plate has a shape adapted to match the contour at least a portion of the spinal fixation plate.

8. The spinal fixation kit of claim 1, wherein each base plate includes a mating element formed thereon for mating with the spinal fixation plate.

9. The spinal fixation kit of claim 8, wherein the mating element is formed on a distal surface of each base plate.

10. The spinal fixation kit of claim 9, wherein each mating element comprises a protrusion that is oriented at an angle so that each mating element is effective to grasp the spinal fixation plate when the arms are moved either away from or toward one another.

11. The spinal fixation kit of claim 1, further comprising an adjustment mechanism formed on the proximal end of the second arm and effective to allow movement of the second arm along the support member.

12. The spinal fixation kit of claim 11, wherein the adjustment mechanism comprises a box-shaped member having a spring-lock mechanism that is movable between a first, locked position, and a second position wherein the second arm is slidable along the support member.

13. The spinal fixation kit of claim 11, wherein the adjustment mechanism comprises threads that are effective to mate with corresponding threads formed on the support member such that rotation of the support member is effective to move the second arm with respect to the first arm.

* * * * *